United States Patent [19]

Wilke et al.

[11] 4,080,388

[45] * Mar. 21, 1978

[54] PHENYL SUBSTITUTED-HEXENE-(3)-DIOL-(1,6)

[75] Inventors: Günther Wilke; Paul Heimbach, both of Mulheim an-der-Ruhr, Germany

[73] Assignee: Studiengesellschaft Kohle mbH, Mulheim an der Ruhr, Germany

[ * ] Notice: The portion of the term of this patent subsequent to May 4, 1993, has been disclaimed.

[21] Appl. No.: 621,187

[22] Filed: Oct. 9, 1975

Related U.S. Application Data

[62] Division of Ser. No. 424,230, Dec. 12, 1973, Pat. No. 3,954,887, which is a division of Ser. No. 64,845, Jul. 29, 1970, Pat. No. 3,832,371, which is a division of Ser. No. 678,172, Oct. 26, 1967, Pat. No. 3,544,604.

[30] Foreign Application Priority Data

May 26, 1967 Germany ............................ St 26928

[51] Int. Cl.² ............................................. C07C 43/20
[52] U.S. Cl. ............................. 260/613 R; 260/618 R
[58] Field of Search ....................... 260/618 R, 613 R

[56] References Cited

U.S. PATENT DOCUMENTS

| | | | |
|---|---|---|---|
| 2,850,539 | 9/1958 | Schott et al. | 260/613 R X |
| 2,911,445 | 11/1959 | Friederich | 260/618 R X |
| 3,198,841 | 8/1965 | Kochi | 260/618 R |
| 3,954,887 | 5/1976 | Wilke et al. | 260/618 R |

OTHER PUBLICATIONS

Wittig et al., Chem. Abs., vol. 30 (1936) 8200.
S. Kohle m.b.H., Chem. Abs., vol. 71 (1969) 123910v.

*Primary Examiner*—Bernard Helfin
*Attorney, Agent, or Firm*—Burgess, Dinklage & Sprung

[57] ABSTRACT

Process of producing nickel alcoholates by reacting π-allyl nickel compounds with carbonyl compounds. The nickel alcoholates so produced can be hydrolyzed to their corresponding alcohols and these alcohols can in part be dehydrated to their corresponding olefins. The nickel alcoholate products are useful for the production of their corresponding alcohols and these alcohols are useful for the production of their corresponding olefins.

2 Claims, No Drawings

PHENYL SUBSTITUTED-HEXENE-(3)-DIOL-(1,6)

This is a division, of application Ser. No. 424,230, filed Dec. 12, 1973, now U.S. Pat. No. 3,954,887, which, in turn, is a divisional application of Ser. No. 64,845, filed July 29, 1970, now U.S. Pat. No. 3,832,371, which, in turn, is a divisional application of Ser. No. 678,172, filed Oct. 26, 1967, now U.S. Pat. No. 3,544,604.

This invention relates to novel nickel alcoholates and alcohols thereof and to process of preparing said novel nickel alcoholates and alcohols.

According to German Pat. No. 1,191,375, it is possible to prepare complexes of transition metals by reducing compounds of transition metals with organometallic compounds of the metals of Groups I to III of the Periodic Table in the Presence of electron donors. This process permits also the preparation of complexes of zero-valent nickel such as all-trans-cyclododecatri-1,5,9-ene-nickel (O), bis(cyclooctadi-1,5-ene)-nickel (O), cyclooctatetraene-nickel (O), tetrakis(triphenylphosphine)nickel (O).

In further developing this process, it has been found that, in displacement reactions, the ligands bonded to the central metal may be replaced by other ligands. For example, all-trans-cyclododecatri-1,5,9-ene-nickel (O) reacts at as low as about $-60°$ C with butadiene. Thereby, the cyclododecatriene is displaced and there is formed a $C_{12}$-bis-$\pi$-allyl system I bonded to nickel by combination of three butadiene molecules each:

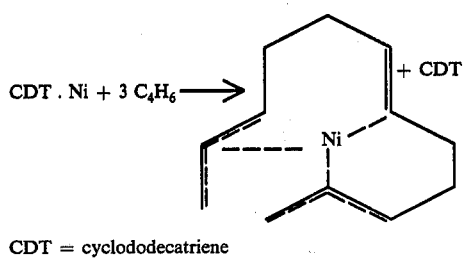

CDT = cyclododecatriene

Furthermore, it has been found that carbonyl compounds, especially unsaturated carbonyl compounds such as benzaldehyde, cinnamic aldehyde, phenyl pentadienal, vitamin A aldehyde, crotonaldehyde, acrolein, mesityl oxide, $\beta$-ionone are capable of entering into displacement reactions of this kind. For example, monocinnamic aldehyde nickel (O) or bis(cinnamic aldehyde nickel (O) is obtained from bis(cyclooctadi-1,5-ene) nickel (O) and cinnamic aldehyde with the cleavage of cyclooctadi-1,5-ene. Analogous products are obtained with other cabonyl compounds.

It has now been found surprisingly that it is possible by the simultaneous action of carbonyl compounds and 1,3-diolefins on complexes of zero-valent nickel to link every two molecules of the carbonyl compound with one molecule of a 1,3-diolefin thereby forming a nickel alcholate of hexene-(3)-diol-(1,6). For example, in a simple case, it is possible to link benzaldehyde and butadiene to form the nickelate of 1,6-diphenylhexene-(3-trans)-diol-(1,6) II according to the following equation:

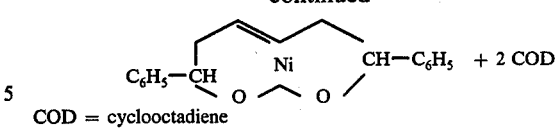

COD = cyclooctadiene

After hydrolysis of the nickelate, the diol which may be converted in known manner into 1,6-diphenylhexatri1,3,5-ene is obtained in high yields.

The proces according to the invention for the production of novel alcohols and nickel alcoholates thereof comprises (a) allowing carbonyl compounds and 1,3-diolefins to act on complexes of nickel (O) or (b) reacting $\pi$-allyl nickel compounds with carbonyl compounds, then hydrolyzing the resultant novel nickel alcoholates in known manner and, if desired, dehydrating the alcohols.

The process of the invention has been found to be generally applicable, i.e. both the carbonyl compounds and the 1,3-diolefins may be varied in any manner. Suitable carbonyl compounds which may be used include aliphatic, alicyclic, saturated and unsaturated aldehydes and ketones and saturated and unsaturated aldehydes and ketones which are substituted by aromatic radicals. Examples include formaldehyde, acetaldehyde, propionaldehyde, butyric aldehyde, acrolein, crotonaldehyde, hexadienal, propargyl aldehyde, benzaldehyde, cinnamic aldehyde, phenylpentadienal, vitamin A aldehyde, anisic aldehyde, vanillin, acetone, methyl ethyl ketone, mesityl oxide, cyclopentanone, cyclohexanone, acetophenone, benzophenone, $\beta$-ionone. Aliphatic, alicyclic saturated and unsaturated dialdehydes and diketones and saturated and unsaturated dialdehydes and diketones which are substituted by aromatic residues may also be used. Examples include glyoxal, malonic dialdehyde, succinic dialdehyde, diacetyl, acetyl acetone, acetonyl acetone, benzil, benzoyl acetone. When using dialdehydes and diketones, longer chains having recurring monomeric units may be formed. Suitable 1,3-diolefins are butadiene or butadienes which are substituted by aliphatic, alicyclic or aromatic radicals such as isoprene, 2,3 -dimethyl butadiene, 2,3-diphenyl butadiene. Both the carbonyl compounds and the 1,3-diolefins may contain functional groups which, however, are groups which are not reactive or react very much slower with the metal atoms than the carbonyl group or 1,3-diolefin grouping. Examples of such functional groups include ether, ester, acetyl, amine and nitrile groupings.

The process of the invention may be advantageously carried out by allowing the carbonyl compounds and the 1,3-diolefins to act directly on the isolated complex compounds of nickel. Another particularly advantageous method of carrying out the process is to reduce nickel compounds such as nickel acetyl acetonate by means of organometallic compounds in the simultaneous presence of carbonyl compounds and 1,3-diolefins according to the process described in German Pat. No. 1,191,375. The nickel atoms obtained during the reduction act then in the same manner as the metal atoms combined in the isolated complexes. This embodiment just mentioned permits the use of catalytic amounts of nickel in performing the reaction which normally proceeds stoichiometrially with respect to nickel because the nickelates being produced during the process of the invention may in turn be reduced. The process remains a stoichiometric reaction with respect to the organometallic component used.

In this reaction according to the invention, π-allyl nickel alcoholates are formed:

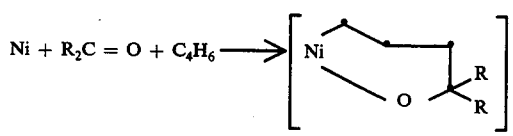

According to the invention, products of this kind may be prepared advantageously from bis-π-allyl compounds of nickel and carbonyl compounds. In this manner, the $C_{12}$ bis-π-allyl compound mentioned above reacts with, for example, benzaldehyde to form a π-allyl nickel alcoholate.

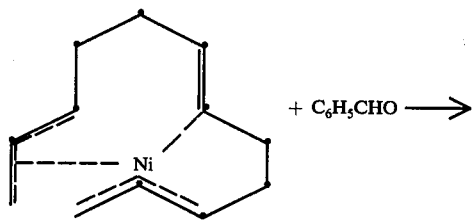

In an analogous manner, π-allyl nickel-1-phenyl-butene(3) -olate (IV) is obtained from bis-π-allyl nickel and benzaldehyde:

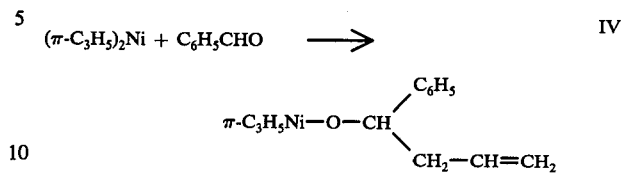

The process according to the invention may be carried out in the presence of solvents such as aliphatic, alicyclic or aromatic hydrocarbons, ethers or esters. However, the carbonyl compounds or the 1,3-diolefins themselves may also serve as solvents. The reaction is carried out at temperatures of from 0° to 200° C and preferably at 20° to 100° C. The nickel alcoholates may either be isolated and subsequently subjected to hydrolysis or directly hydrolyzed without being isolated.

The alcohols obtained by hydrolysis of the nickel alcoholates obtainable by the process according to the invention are valuable starting materials for further syntheses, especially for the production of polyenes. Thus, when starting from vitamin A aldehyde, butadiene and nickel, the process according to the invention gives a nickel alcoholate which, when hydrolyzed, furnishes a diol the dehydration of which leads to a $C_{44}H_{60}$ polyene which is a homologue of beta carotin.

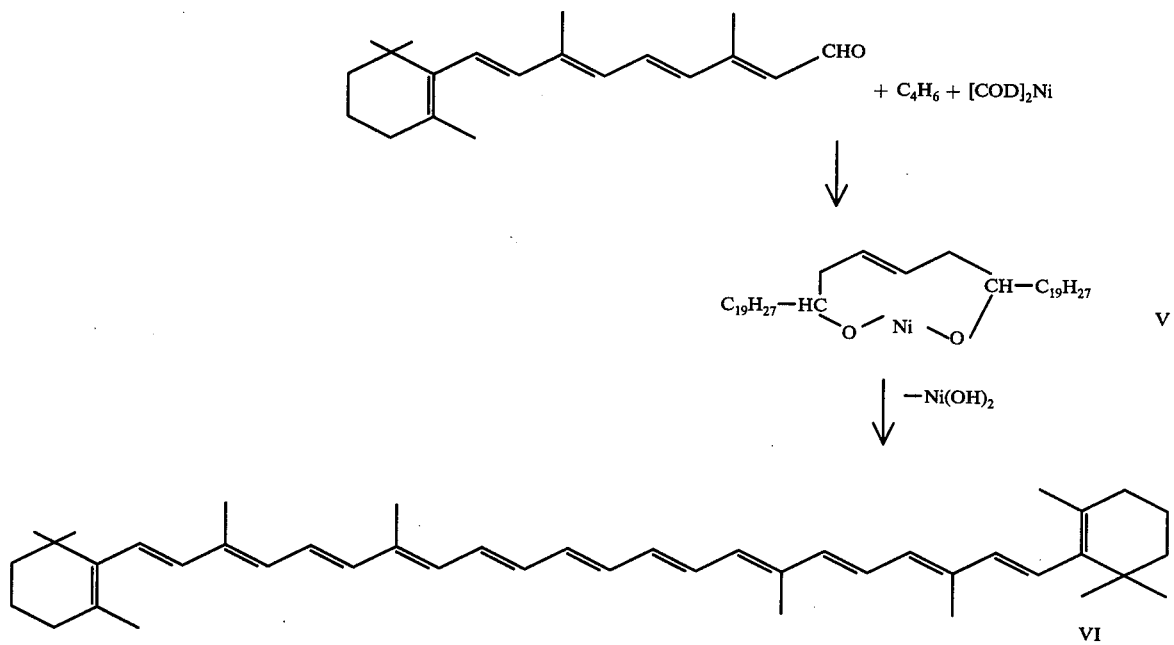

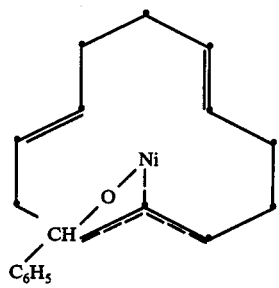

EXAMPLE 1

9.3 Grams = 33.8 mmoles of $(COD)_2Ni$ are suspended in 100 ml. of ether and reacted at −30° C with a solution of 5.0 g. = 113 mmoles of acetaldehyde in ether. Then 3 g. = 55.5 mmoles of butadiene are introduced and the reaction is allowed to proceed at 20° C. After 24 hours, the mixture is filtered. A light violet, sparingly soluble precipitate is obtained. The solution is almost colorless. Yield: 6.4 grams = 31.8 mmoles = 94% of the theory.

$C_8H_{14}O_2Ni$ Calculated, 29.2% Ni; found, 30.1% Ni.

A portion of 3.6 g. = 17.9 mmoles of the alcoholate are reacted with 100 ml of aqueous alcohol (5% of water). After 24 hours, the green suspension is freed from the solvents at $10^{-4}$ mm. Hg. The green residue is extracted with either, the extract is evaporated and the residue distilled; b.p. = 90°-95° C/0.05 mm. Hg. Yield: 2.2 g. of a viscous oil which, according to analysis by gas chromatography, consists of 97% of octene-(4)-diol-(2.7). Yield, 83% of the theory.

EXAMPLE 2

12.2 Grams = 44 mmoles of $(COD)_2Ni$ are suspended in 14.7 g. = 138 mmoles of benzaldehyde and 200 ml. of ether. Immediately thereafter, about 6 g. = 110 mmoles of butadiene are introduced. After 12 hours, 41 mmoles = 92% of the theory of the nickel alcoholate II are obtained as a brown precipitate.

$C_{18}H_{18}O_2Ni$ Calculated, 18.05% Ni; M = 325.01. Found, 17.90% Ni; M = 320.0.

4.2 Grams = 12.9 mmoles of II are dissolved in 50 ml. of benzene and added dropwise to the deep red solution of 2 g. = 26 mmoles of acetyl acetone. The reaction takes place immediately with the color turning green. 2.78 Grams = 10.4 mmoles of 1,6-diphenyl-transhexene-(3)-diol-(1,6) = 80% of the theory are obtained. Melting point, 117°-118° C after recrystallization from benzene/petroleum ether.

$C_{18}H_{20}O_2$ Calculated, 80.56% C; 7.51% H. Found, 80.21% C; 7.62% H.

5 Grams = 18.6 mmoles of diphenyl hexenediol are dehydrated with 5 ml. of $POCl_3$ in 30 ml. of anhydrous pyridine by the process of GREIDINGER and GRINSBERG to give 2.6 g. = 11.2 mmoles = 60% of the theory of 1,6-diphenyl hexatri-1,3,5-ene having a melting point of 200° C after recrystallization from benzene/petroleum ether.

EXAMPLE 3

7.4 Grams = 27 mmoles of $(COD)_2Ni$ are suspended in 100 ml. of benzene. To the suspension are added dropwise 7.3 g. = 55 mmoles of cinnamic aldehyde while vigorously stirring. The brown precipitate dissolves completely upon introduction of 3 g. = 55 mmole of butadiene. Then 5.8 g. = 58 mmoles of acetyl acetone are added and 7 g. = 21.9 mmoles = 81% of the theory of 1,10-diphenyl decatri-1,5,9-ene-diol-(3.8) are isolated. Melting point, 125°-127° C after recrystallization from benzene/petroleum ether.

$C_{22}H_{24}O_2$ Calculated, 82.46% C; 7.59% H. Found, 82.29% C; 7.57% H.

Melting of 3 g. of diphenyl decatrienediol together with 1 g. of freshly annealed potassium bisulfate at 120° C. and extraction of the residue with a boiling mixture of mathanol and benzene gives 1.87 g. = 6.6 mmoles = 70% of the theory of 1,10-diphenyl decapentaene(1,3,5,7,9) melting at 253° C.

EXAMPLE 4

When adding dropwise 16.5 g. = 110 mmoles of phenyl pentadienal to the suspension of 14.3 g. = 52 mmoles of $(COD)_2Ni$ in 100 ml. of benzene, a clear and deep red solution is initially formed. From this solution, crystalline phenyl pentadienal-Ni.COD precipitates. When introducing 7 g. = 129 mmoles of butadiene, the precipitate dissolves slowly with the color turning brown. After 24 hours of reaction, 11.6 g. = 116 mmoles of acetyl acetone are added dropwise and after further 24 hours 7,7 g. = 23.5 mmoles = 45% of the theory of light yellow crystalline 1,14-diphenyl-tetradecapentaene(1,3,7,11,13)-diol-(5,10) are isolated.

$C_{26}H_{28}O_2$ Calculated, 83.83% C; 7.59% H. Found, 83.39% C; 7.62% H.

1.0 Gram = 3 mmoles of diphenyl tetradecapentaene diol are heated with freshly annealed potassium bisulfate for 2 hours at 170° C. Thereafter, the mixture is thoroughly washed with hot water and repeatedly boiled with benzene and chloroform. Upon cooling, 0.6 g. = 2.4 mmoles = 80% of the theory of 1,14-diphenyl-tetradecaheptaene-(1,3,5,7,9,11,13) precipitate. Melting point, 277° C after recrystallization from chloroform.

EXAMPLE 5

A solution of 6.5 g. = 22.8 mmoles of vitamine A aldehyde in benzene was added dropwise to 3.1 g. = 11.27 mmoles of $(COD)_2Ni$ in 100 ml. of benzene. 3.4 Grams = 62.8 mmoles of butadiene are introduced into the red solution. After a reaction time of 4 days, the solvents are removed at $10^{-4}$ mm. Hg, the brown residue suspended in 100 ml. of aqueous alcohol (5% of water) and the $Ni(OH)_2$ removed. 7.3 Grams of $C_{44}$ diol in the form of an orange oil are obtained as residue.

A solution of 7.3 g. of $C_{44}$ diol in 70 ml. of boiling benzene is mixed with 250 mg. of N-bromosuccinimide. After a few seconds, the yellow solution turns dark red. At the same time, water condenses in the reflux condenser. After further 3 minutes at 80° C, the mixture is cooled, diluted with 300 ml. of petroleum ether and successively washed with solutions of potassium iodide, sodium thiosulfate and sodium chloride. Drying of the solution over sodium sulfate and concentration gives 7.3 g. of an oil which is dissolved in 18 l ml. of benzene/ethanol while hot. At 0° C, 1.0 gram of $C_{44}$ hydrocarbon precipitates which is repeatedly recrystallized from benzene/ethanol. Yield, 1.0 g. = 1.7 mmoles of $C_{44}H_{60}$ = 15%, based on $(COD)_2Ni$ charged. Melting point, 194°-196° C.

EXAMPLE 6

A suspension of 11.9 g. = 43.4 mmoles of $(COD)_2Ni$ in 100 ml. of acetone is prepared. Into the suspension, 6.0 g. = 11 mmoles of butadiene are introduced at room temperature. Thereby, the yellow suspension turns dark red. After stirring for two days, the color of the reaction mixture turns green. At the same time, the contents of the flask solidify to form a gel. The volatile constituents are distilled off at 0.5 mm. Hg to leave 10.7 g. of a solid residue which is extracted in a soxhlet for 48 hours with 100 ml. of ether. The residue sublimes at $10^{-4}$ mm. Hg and 70° C. There are obtained 4.5 g. = 26 mmols = 60% (based on nickel charged) of 2,7-dimethyloctene-(4)-diol-(2,7). Melting point, 85°-86° C.

$C_{10}H_{20}O_2$ Calculated, 69.72% C; 11.70% H; M = 172.20. Found, 69.72% C; 11.4% H; M = 172.

When carrying out the reaction at 70° C in a bomb tube, the same conversion is obtained in about 5 hours. The results correspond to those of the preceding experiments.

EXAMPLE 7

11 Grams = 20 mmoles of butadiene are introduced into a suspension of 19.55 g. = 71 mmoles of $(COD)_2Ni$ and 125 ml. of cyclohexanone. After as little as about 4 hours, the color turns green. The green gel-like reaction mixture is diluted with 100 ml. of ether, shaken with 50 ml. of 2N $H_2SO_4$ and washed with $NaHCO_3$ until it is free from acid. After drying over anhydrous $Na_2SO_4$, excess butadiene and the ether are distilled off from the colorless solution. Recrystallization of the residue remaining after distillation from benzene/petroleum ether gives 11.6 g. = 46 mmoles = 65% of the theory of colorless 1,4-di(cyclohexanolyl-1)butene-(2) having a melting point of 101° C.

$C_{16}H_{28}O_2$ Calculated, 76.14% C; 11.10% H. Found, 76.59% C; 11.02% H.

EXAMPLE 8

12.0 Grams = 22 mmoles of butadiene are introduced into a suspension of 20.4 g. = 74 mmoles of $(COD)_2Ni$ in 100 ml. of acetophenone. The $(COD)_2Ni$ dissolves while the color turns red. After stirring for three days at about 20° C, the gel-like reaction mixture which is now green is diluted with 200 ml. of ether, washed with 50 ml. of 2N $H_2SO_4$, neutralized with a $NaHCO_3$ solution and dried over $Na_2SO_4$. After several days, 3 grams of 1-methyl-(1,3,5)-triphenyl-(2)-benzoylcyclohexadiene-(2,4) precipitate from the yellow solution. Melting point, 136° C after recrystallization from methanol.

$C_{32}H_{26}O$ Calculated, 90.01% C; 6.14% H. Found, 89.89% C; 6.20% H.

At $10^{-4}$ mm. Hg and about 20° C, butadiene, COD and acetophenone are removed as far as possible from the mother liquor. There remain still 39.5 grams from which a yellow liquid can be distilled off at $10^{-4}$ mm. Hg and a bath temperature of 140°-150° C, this liquid consisting of 89% of dypnone.

From the residue remaining at 150° C, 14 g. = 63% of the theory of 2,7-diphenyl-octene-(4)-diol-(2,7) are obtained. Melting point, 114° C after recrystallization from benzene petroleum ether.

$C_{20}H_{24}O_2$ Calculated, 81.04% C; 8.16% H. Found, 81.22% C; 8.02% H.

EXAMPLE 9

6.8 Grams = 100 mmoles of isoprene are added dropwise at 20° C, to a suspension of 11.6 g. = 42 mmoles of $(COD)_2Ni$ in 52 g. = 49.3 mmoles of benzaldehyde and 50 ml. of alcohol (5% of water) while stirring. The reaction begins instantaneously and the temperature rises to about 40° C with the mixture becoming solid like a gel. There are obtained 7.5 g. = 26.6 mmoles = 63% of the theory of 1,6-diphenyl-(3)-methyl-hexene-(3)-diol-(1,6) having a melting point of 125°-126° C.

$C_{19}H_{22}O_2$ Calculated, 80.81% C; 7.81% H. Found, 81.08% C; 7.98% H.

EXAMPLE 10

8.8 Grams = 107 mmoles of 2,3-dimethyl butadiene are added dropwise to a mixture of 13.1 g. = 47 mmoles of $(COD)_2Ni$ in 52 g. = 493 mmoles of benzaldehyde and 50 ml. of alcohol (5% of water). The color change occurs after 3 hours. After further 24 hours, 6.9 g. = 23.3 mmoles = 50% of the theory of 1,6-diphenyl-(3,4)-dimethylhexene-(3)-diol-(1,6) having a melting point of 129°-130° C are obtained.

$C_{20}H_{24}O_2$ Calculated, 81.04% C; 8.16% H. Found: 81.41% C; 8.19% H.

EXAMPLE 11

A solution of 1.1 g. = 10 mmoles of benzaldehyde and 1.0 g. = 46 mmoles of 2,3-diphenyl butadiene in 10 ml. of benzene is added dropwise to a suspension of 1.0 g. = 36 mmoles of $(COD)_2Ni$ in 30 ml. of benzene. After 24 hours, 1.0 g. = 10 mmoles of acetyl acetone is added to the dark red solution whereupon the color of the solution turns green through brown. 0.7 Grams = 1.7 mmoles = 47% of the theory of 1,3,4,6-tetraphenyl-hexene-(3)-diol-(1,6) having a melting point of 134°-135° C could be isolated.

$C_{13}H_{28}O_2$ Calculated, 85.67% C; 6.71% H. Found: 85.65% C; 6.88% H.

EXAMPLE 12

A solution of 3.3 g. = 23.4 mmoles of bis($\pi$-allyl)-nickel in 100 ml. of ether is reacted at 0° C with 2.5 g. = 23.5 mmoles of benzaldehyde. The mixture turns dark red. After 12 hours, the volatile constituents are removed at $10^{-4}$ mm. Hg. The residue weighing 5.1 g. is dissolved in 40 ml. of pentane and recrystallized at $-80°$ C. Yield: 3.5 g. = 14.1 mmoles of $\pi$-allyl-nickel-1-phenylbutene-(3)-olate = 60% of the theoretical yield.

$C_{13}H_{16}O$ Ni Calculated, 23.8% Ni; M = 246.5. Found, 24.1% Ni; M = 498.

3.5 Grams = 14.1 mmoles of the alcoholate are reacted with 100 ml. of alcohol (5% of water). After 24 hours, the green suspension is freed from the solvents at $10^{-4}$ mm. Hg. The green residue is extracted with ether and the extract evaporated. There are obtained 1.8 g. of a viscous oil having a boiling point of 96°-97° C/0.5 mm. Hg and consisting of 96% of 1-phenylbutene-3-ol according to analysis by gas chromatography. Yield. 82% of the theoretical.

EXAMPLE 13

A suspension of 11 g. = 40 mmoles of $(COD)_2Ni$ in 100 ml. of benzene is prepared and reacted with 11 g. = 80.8 mmoles of anisic aldehyde. Thereafter, about 6 g. = 110 mmoles of butadiene are introduced. After 24 hours, a brown precipitate is formed and, after removal of the solvent, reacted with 100 ml. of alcohol (5% of water). After 24 hours, the green suspension is freed from the solvents at $10^{-4}$ mm. Hg. The residue is extracted with ether and the extract evaporated to give 9.8 g. = 29.8 mmoles of 1,6-bis(4-methoxyphenyl)-hexene-(3)-diol-(1,6) = 74% of the theory. Melting point, 140°-141° C after recrystallization from benzene and petroleum ether.

$C_{20}H_{24}O_4$ Calculated, 73.14% C; 7.36% H. Found: 73.00% C; 7.20% H.

EXAMPLE 14

A solution is prepared from 49.5 mmoles of $C_{12}H_{18}$.Ni (I) and butadiene in 200 ml. of ether and mixed at 20° C with 15 g. = 141 mmoles of benzaldehyde. A light brown voluminous precipitate separates immediately. After 12 hours, 4.8 g. = 14.7 mmoles = 29.6% of the theory of the sparingly soluble compound (III) are isolated.

$C_{19}H_{24}Ni$ Calculated, 17.9% Ni; found, 18.5% Ni.

A suspension of 2.5 g. = 7.6 mmoles of III in 30 ml. of benzene is prepared. When adding 15 ml. of glacial acetic acid, a deep red solution is formed which, after addition of about 0.1 g. of $PtO_2$, is subjected to catalytic hydrogenation at 50 atm. The product is processed after 24 hours. At $10^{-4}$ mm. Hg and 135°-145° C, 1.4 g. of 1-phenyltridecanol(1) distil as a viscous oil. Yield, 67% of the theoretical.

EXAMPLE 15

Preparation of 1,6di(p-dimethylaminophenyl)-trans-3-hexene-1,6-diol

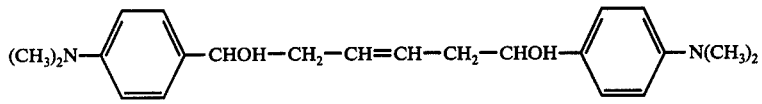

EXAMPLE 16

Preparation of 1,6-di(2-furyl)-trans-3-hexene-1,6-diol

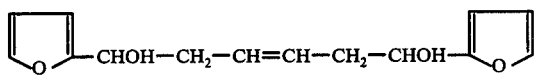

4 Grams = 74.0 mmoles of butadiene are introduced into a suspension of 10 g. = 36.4 mmoles of bis(cyclooctadiene)nickel in 70 ml. of ether. Then 7 g. = 72.8 mmoles of furfural are added at a time and the mixture stirred for 24 hours at 20° C. The nickel alcoholate is formed as a wine-red precipitate which is removed by filtration and washed with ether. The diol is liberated with the corresponding amount of acetyl acetone whereby nickel acetyl acetonate is obtained. Processing of the ether solution gives 4.8 g. of raw product. Crystallization from benzene gives 4.2 g. of needleshaped crystals having a melting point of 108° C. this yield corresponding to 46.8%, based on bis(cyclooctadiene)-nickel charged. The structure of the compound is confirmed by the IR and NMR spectra.

C, H analysis: $C_{14}H_{16}O_4$ Calculated, 67.7% C; 6.49% H. Found, 68.2% C; 6.52% H.

4.6 Grams = 85 mmoles of butadiene are introduced into a suspension of 10 g. = 36.4 mmoles of bis(cyclooctadiene)nickel and then 10.8 g. = 72.8 mmoles of p-dimethylamino-benzaldehyde are added. The mixture is stirred for 16 hours at 20° C. Then the precipitated nickel alcoholate is separated by filtration, washed and the diol liberated with the corresponding amount of acetyl acetone. Nickel acetyl acetonate is removed by filtration and the yellow ether solution decolorized with animal charcoal to give 5.8 g. of a crystalline raw product and, after recrystallization from ether, 5 g. of the compound $C_{22}H_{30}N_2O_2$ corresponding to 39% of the bis(cyclooctadiene)nickel charged. Melting point, 120°–122° C (dec.). The structure is confirmed by IR and NMR spectra.

The alcohols obtained when hydrolyzing the nickel alcoholates which can be prepared by the process of this invention and being alpha, omega bifunctional alcohols are useful for the preparation of polyesters with the particular possibility to cross-link the resultant polyesters by means of the double bonds which are still contained in the bifunctional alcohols. Thus, any of the alcohols mentioned in the examples and in the specification may be used directly and the nickel alcoholates as preliminary products for the production of polyesters.

What is claimed is:

1. 1,3,4,6-Tetraphenylhexene-(3)-diol-(1,6).
2. 1,6-Bis(4-methoxyphenyl)-hexene-(3)-diol-(1,6).

| C,H analysis: | C | H | N |
|---|---|---|---|
| Calculated for $C_{22}H_{30}N_2O_2$: | 74.6% | 8.54% | 7.90% |
| Found: | 75.1% | 8.62% | 7.85% |